(12) United States Patent
Selvitelli et al.

(10) Patent No.: US 8,038,484 B2
(45) Date of Patent: Oct. 18, 2011

(54) ECG ELECTRODE CONNECTOR

(75) Inventors: David Selvitelli, Suffield, CT (US);
Peter Meyer, Shrewsbury, MA (US)

(73) Assignee: Tyco Healthcare Group LP, Mansfield, MA (US)

( * ) Notice: Subject to any disclaimer, the term of this patent is extended or adjusted under 35 U.S.C. 154(b) by 215 days.

(21) Appl. No.: 12/330,550

(22) Filed: Dec. 9, 2008

(65) Prior Publication Data

US 2009/0149731 A1 Jun. 11, 2009

Related U.S. Application Data

(60) Provisional application No. 61/012,825, filed on Dec. 11, 2007.

(51) Int. Cl.
*H01R 4/48* (2006.01)

(52) U.S. Cl. ........................................ 439/729; 439/909

(58) Field of Classification Search .................. 439/729, 439/261, 268, 859, 909, 835, 838; 600/372; 607/152

See application file for complete search history.

(56) References Cited

U.S. PATENT DOCUMENTS

| | | | | |
|---|---|---|---|---|
| 5,454,739 | A | * | 10/1995 | Strand ........................... 439/729 |
| 5,624,281 | A | * | 4/1997 | Christensson ................ 439/729 |
| 5,944,562 | A | | 8/1999 | Christensson |
| 7,083,480 | B2 | * | 8/2006 | Silber ........................... 439/835 |

OTHER PUBLICATIONS

Tyco Healthcare Kendall: ECG Electrodes Where Quality Leads.

* cited by examiner

*Primary Examiner* — Edwin A. Leon
(74) *Attorney, Agent, or Firm* — Lisa E. Winsor, Esq.

(57) ABSTRACT

Disclosed is an ECG electrode lead wire connector which provides improved electrical and mechanical coupling of the ECG electrode press stud to the lead wire, provides enhanced ergonomics to the clinician, and may alleviate patient discomfort associated with the attachment and removal of ECG leads. The connector may be engaged and disengaged with little or no force imparted to the patient or the ECG pad, which significantly minimizes the risk of inadvertent dislodgement of the pad. In one embodiment the disclosed connector provides a thumb cam lever which affirmatively engages the press stud to the connector, and provides tactile feedback to the clinician that the connector is properly engaged. In other embodiments, the connector provides a pushbutton to enable the clinician to easily engage and disengage the connector from the ECG stud. The disclosed connectors may also decrease clinician fatigue, and may provide more reliable ECG results.

13 Claims, 15 Drawing Sheets

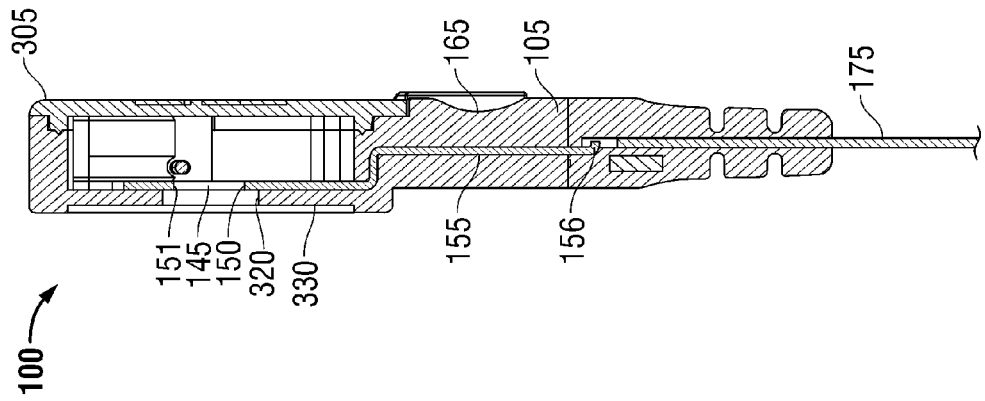
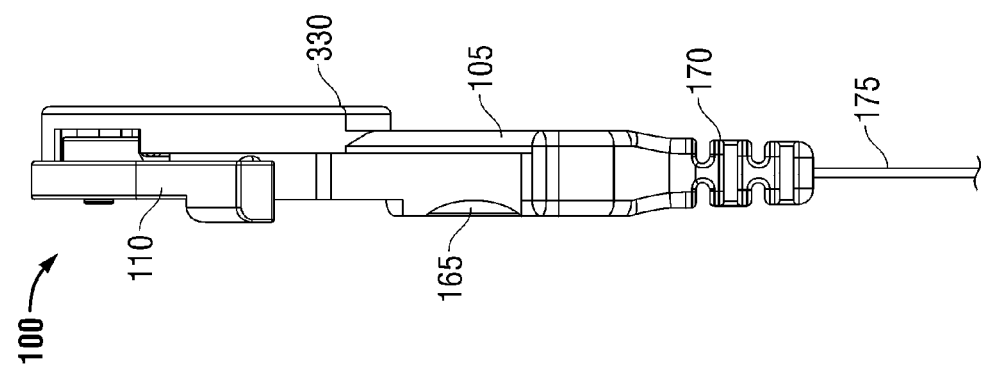

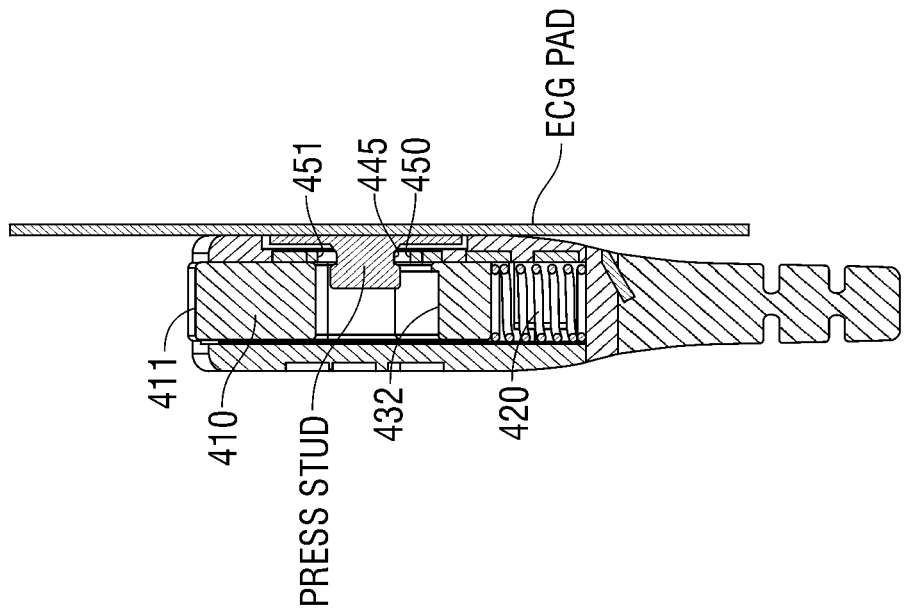
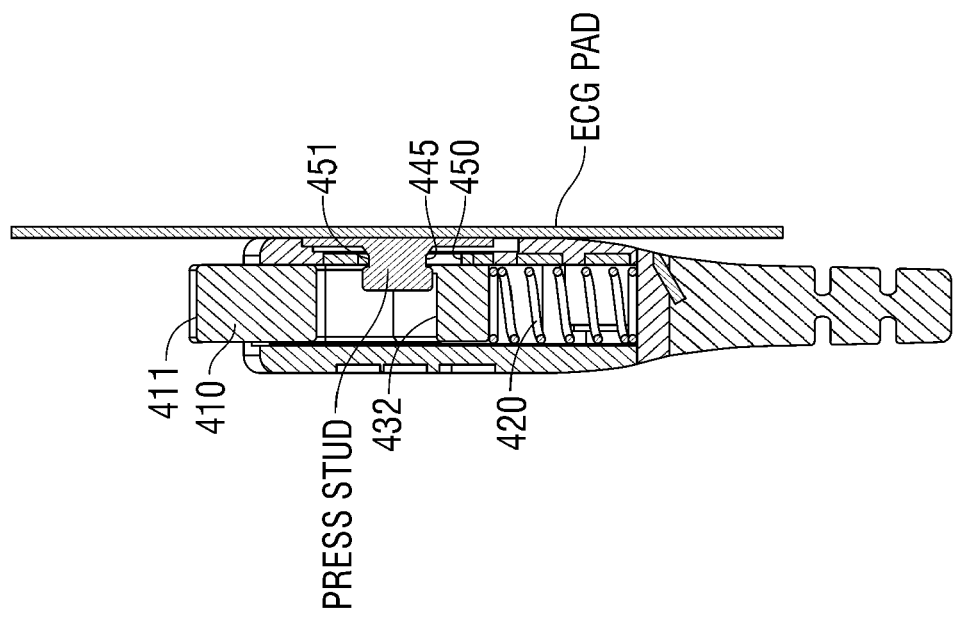

ECG ELECTRODE CONNECTOR

CROSS-REFERENCE TO RELATED APPLICATION

This application claims priority to U.S. Provisional Application Ser. No. 61/012,825, filed Dec. 11, 2007, the entirety of which is hereby incorporated by reference herein for all purposes.

BACKGROUND

1. Technical Field

The present disclosure relates to biomedical electrodes, and in particular, to a biomedical electrode connector for attaching a lead wire to an electrocardiogram (ECG) electrode placed on a patient's body.

2. Background of Related Art

Electrocardiograph (ECG) monitors are widely used to obtain medical (i.e. biopotential) signals containing information indicative of the electrical activity associated with the heart and pulmonary system. To obtain medical signals, ECG electrodes are applied to the skin of a patient in various locations. The electrodes, after being positioned on the patient, connect to an ECG monitor by a set of ECG lead wires. The distal end of the ECG lead wire, or portion closest to the patient, may include a connector which is adapted to operably connect to the electrode to receive medical signals from the body. The proximal end of the ECG lead set is operably coupled to the ECG monitor and supplies the medical signals received from the body to the ECG monitor.

A typical ECG electrode assembly may include an electrically conductive layer and a backing layer, the assembly having a patient contact side and a connector side. The contact side of the electrode pad may include biocompatible conductive gel or adhesive for affixing the electrode to a patient's body for facilitating an appropriate electrical connection between a patient's body and the electrode assembly. The connector side of the pad may incorporate a metallic press stud having a bulbous profile for coupling the electrode pad to the ECG lead wire. In use, the clinician removes a protective covering from the electrode side to expose the gel or adhesive, affixes the electrode pad to the patient's body, and attaches the appropriate ECG lead wire connector to the press stud by pressing or "snapping" the lead wire connector onto the bulbous press stud to achieve mechanical and electrical coupling of the electrode and lead wire. After use, a clinician then removes the ECG lead wire connector from the pad by pulling or "unsnapping" the connector from the pad.

The described ECG lead wire connector may have drawbacks. A clinician must apply considerable downward force on the lead wire connector to achieve positive engagement of the connector to the press stud. This high connecting force may cause additional and unnecessary discomfort or pain to the patient, whose existing medical condition may already be a source of discomfort or pain. A patient's discomfort may be compounded by the need to connect multiple electrodes which are customarily employed during ECG procedures.

Upon completion of the ECG procedure, a clinician must unsnap the ECG lead wire connector from the pad, which may further cause discomfort to the patient. In some instances, the connector does not readily disengage from the press stud thus requiring the clinician to use considerable upward force to unseat the connector. Often, these attempts to decouple the ECG lead wire connector from the electrode press stud will instead cause the pad to be suddenly and painfully torn from the patient's skin. In other instances, attempts to detach the ECG lead wire will cause the pad to become partially dislodged from the patient, which may impair the electrode's ability to receive biopotential signals. This is undesirable when, for example, the clinician wishes to detach the lead wires temporarily yet wishes to leave the pads in place to perform ECG testing on the patient at a future time.

In yet other instances, a snap lock connector may engage the press stud with insufficient force, which may cause suboptimal signal transmission from the electrode to the lead wire, as well as allowing the connector to be disengaged inadvertently by, for example, a slight tug on the lead wire. These effects are undesirable, because they may invalidate the ECG procedure, requiring time-consuming re-testing of the patient, or may lead to delayed, inaccurate or unreliable test results.

Additionally, the process of snapping and unsnapping lead wire connectors from ECG pads, while simultaneously striving to avoid the above-mentioned adverse effects, requires considerable manual dexterity on the part of the ECG clinician. Since clinicians typically repeat the electrode connection/disconnection routine many times each day, the described drawbacks may lead to clinician discontentment and fatigue.

SUMMARY

In an embodiment in accordance with the present disclosure, there is provided an ECG lead wire connector which includes a housing and a thumb cam lever having an open and a closed position. In the open position, the press stud of an ECG electrode assembly may be inserted into a mating receptacle provided in the housing, optionally using insignificant or no insertion force. Once placed in position, the thumb cam lever may be moved to the closed position, thereby positively coupling the press stud and connector without imparting undesirable force to the ECG electrode pad or to the patient. Detents may be provided by the disclosed lever to provide positive locking of the connector in the closed position to achieve optimal electrical coupling between the press stud and the connector, and additionally to provide tactile feedback to the clinician that the thumb cam lever is properly locked.

The connector may include a spring member which biases the thumb cam lever in the direction of the open position when the lever is unlocked. The spring member is configured to operably engage the narrow "waist" portion of the bulbous press stud when the thumb cam lever is in the closed position. When the thumb cam lever is in the closed position, the spring member biases the press stud against a mating electrical contact member provided within the connector housing to electrically couple the press stud and the contact member, and to achieve positive mechanical coupling of the press stud and the connector housing. The electrical contact member is operably coupled to the distal end of a lead wire by any suitable means, such as soldering, crimping, welding, or wire bonding. The proximal end of the lead wire may terminate in any suitable manner, such as to a connector, for operably coupling the lead wire to an ECG monitor. The lead wire may be supported at its exit point from the housing by a strain relief.

In another embodiment according to the present disclosure, an ECG lead wire connector is provided which includes a housing, and a pushbutton having an external face and an internal engaging surface. The pushbutton is biased by a spring member toward a locked position when released (i.e., when no pressure is applied to the pushbutton), and having an unlocked position when depressed (i.e., when sufficient pressure is applied to the face of the pushbutton by, for example, a clinician). A receptacle adapted to accept an electrode pad press stud is provided within the connector housing. When the pushbutton is depressed, the engaging surface thereof is configured to allow the insertion of a press stud into the receptacle, optionally using insignificant or no insertion force. Once the press stud is inserted, the pushbutton may be released, which causes the spring member to bias the engaging surface of the pushbutton against the press stud, engaging the press stud and a mating electrical contact member provided within the connector housing, to electrically couple the press stud and the contact member, and to achieve positive mechanical coupling of the press stud and the connector housing.

In one embodiment envisioned within the scope of the present disclosure, the pushbutton face may be positioned at the distal end of the connector housing. The spring member may be a coil spring positioned between the proximal end of the pushbutton and a corresponding saddle provided within the connector housing. The engaging surface is defined by an opening provided within the central portion of the pushbutton.

In another embodiment contemplated by the present disclosure, the pushbutton is a pivoting lever having at one end an external face positioned at the central region of the connector housing, and at the opposite end an engaging surface for engaging the press stud. The spring member may be a leaf spring positioned at the face end of the lever, between the housing and the lever, such that the lever face end is biased outwardly from the housing. Additionally or alternatively, the leaf spring may be positioned at the clamping end of the lever.

In the various embodiments, it is envisioned the electrical contact member provides a contact opening to receive the press stud. The opening may have narrow end and a wide end. For example, the opening may have an ovoid shape exhibiting one axis of symmetry ("egg-shaped"). Alternatively, the contact opening may be pear-shaped, keyhole-shaped, circular, or described by the intersection of two partially-coincident circles of differing radii. The opening may be dimensioned at its wide end to accept the bulbous press stud, optionally with insignificant or no interference. Conversely, the narrow end of the opening may be dimensioned to capture the narrow waist portion of the press stud. The contact opening may be configured such that, when engaged, the press stud is biased and/or clamped against the narrow end of the contact opening.

It should be understood that the spring members disclosed herein are not limited to coil and/or leaf springs, and may include any suitable source of biasing force, including without limitation gas springs, pressure- or vacuum-actuated devices, elastomeric springs, magnetic or electromagnetic devices, shape memory alloy motors, and other sources of biasing force as will be familiar to the skilled practitioner. Additionally or alternatively, the spring members may be integrally formed with, for example, the housing, lever, or pushbutton.

Other embodiments are envisioned within the present disclosure, such as an ECG lead wire connector having a plurality of pushbuttons, for example, that are disposed on opposite sides of the housing, wherein at least one button is operable to engage and disengage the press stud of an ECG pad.

Alternative modalities of press stud engagement are envisioned wherein, for example, the pushbutton operates in a push-on/push off fashion. In this arrangement, the connector is initially provided in an open or unlocked configuration. The press stud may then be inserted into the receptacle, optionally with insignificant or no insertion force. Once in place, the press stud may be engaged by pressing the pushbutton in a first push-on step. To disengage the press stud, the pushbutton is depressed a second time to release the press stud in a second push-off step and to reset the connector to the initial state, thereby readying the connector for subsequent use. In another modality of press stud engagement, the connector includes a source of biasing force, such as a spring member, that is configured to automatically engage a press stud upon detection of a triggering event, such as the insertion of a press stud into the connector. To disengage the press stud, a release control, such as a pushbutton or lever, is provided such that when said release control is actuated (i.e., pressed or moved), the press stud is released and/or ejected from the housing. It is further contemplated that actuating the release control resets the connector to the initial state, thereby readying the connector for subsequent use. Still other modalities of disengagement are contemplated where, for example, the press stud may be disengaged by pushing, pulling, twisting or otherwise moving the connector housing.

BRIEF DESCRIPTION OF THE DRAWINGS

Various embodiments of the presently disclosed ECG electrode connector are disclosed herein with reference to the drawings, wherein:

FIG. 3C is a side view of the FIG. 1 embodiment of an ECG electrode connector in accordance with the present disclosure;

FIG. 3D is a side cutaway view of the FIG. 1 embodiment of an ECG electrode connector in accordance with the present disclosure;

FIG. 6C is a side cutaway view of the FIG. 4 embodiment of an ECG electrode connector having a pushbutton in a released position in accordance with the present disclosure;

FIG. 6D is a side cutaway view of the FIG. 4 embodiment of an ECG electrode connector having a pushbutton in a depressed position in accordance with the present disclosure;

DETAILED DESCRIPTION OF EMBODIMENTS

Figure 2:
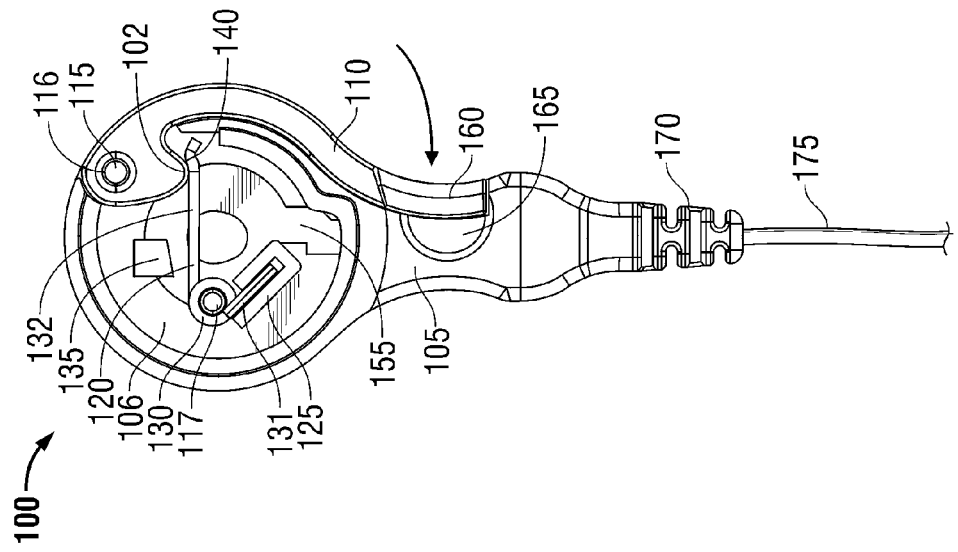
FIG. 2 illustrates the ECG connector of FIG. 1 having a thumb cam lever in a closed position in accordance with the present disclosure.

Embodiments of the presently disclosed ECG electrode connector and method are described herein in detail with reference to the drawings, in which like reference numerals designate identical or corresponding elements in each of the several views. As shown in the drawings and as described throughout the following description, and as is traditional when referring to relative positioning on an object, the term "proximal" refers to the end of the apparatus which is closer to the monitor and the term "distal" refers to the end of the apparatus which is further from the monitor. In the following description, well-known functions or constructions are not described in detail to avoid obscuring the present disclosure in unnecessary detail.

Figure 1:
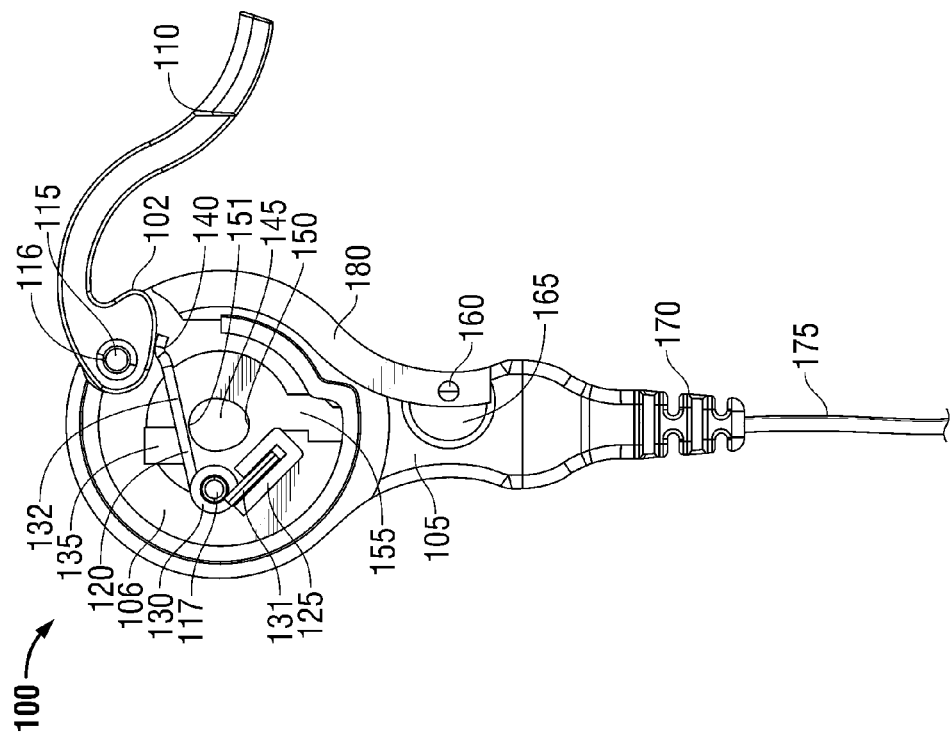
FIG. 1 is a schematic diagram of an embodiment of an ECG electrode connector in accordance with the present disclosure having a thumb cam lever in an open position.
Figure 3B:
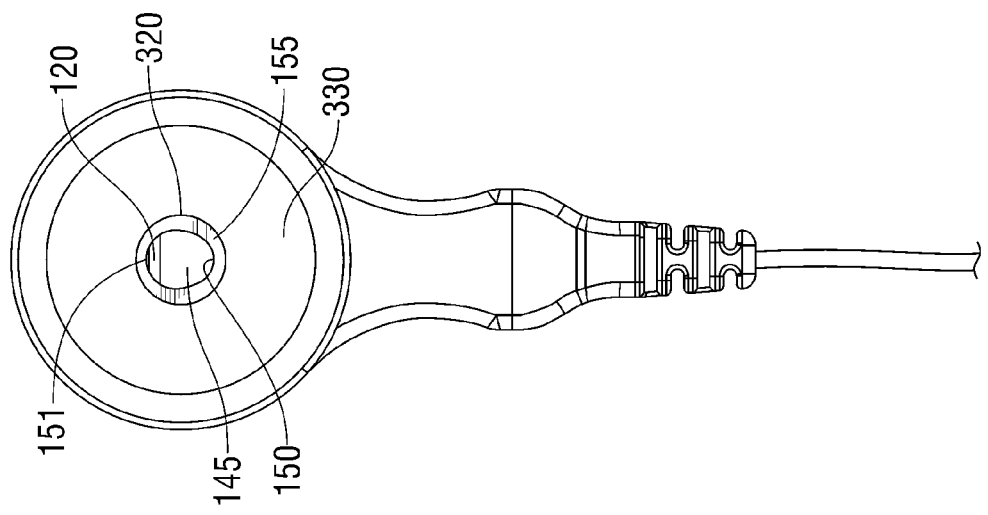
FIG. 3B is a bottom view of the FIG. 1 embodiment of an ECG electrode connector in accordance with the present disclosure.
Figure 3A:
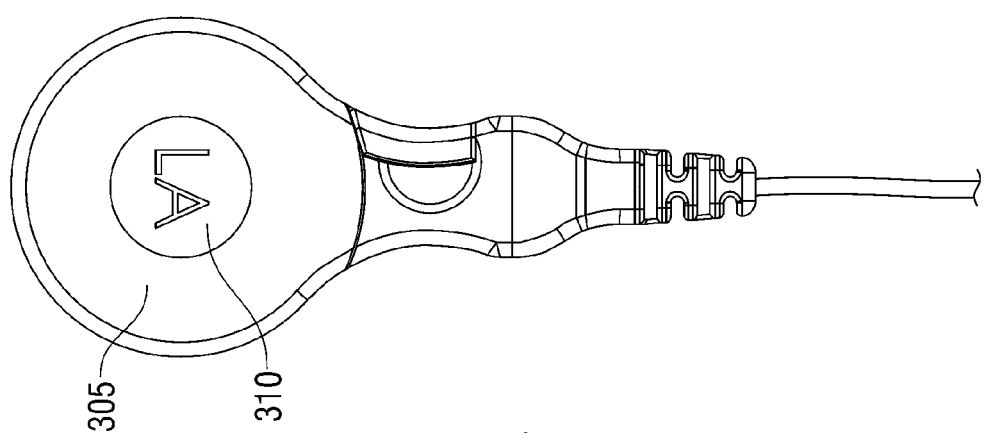
FIG. 3A is a top view of the FIG. 1 embodiment of an ECG electrode connector in accordance with the present disclosure.
Figure 3E:
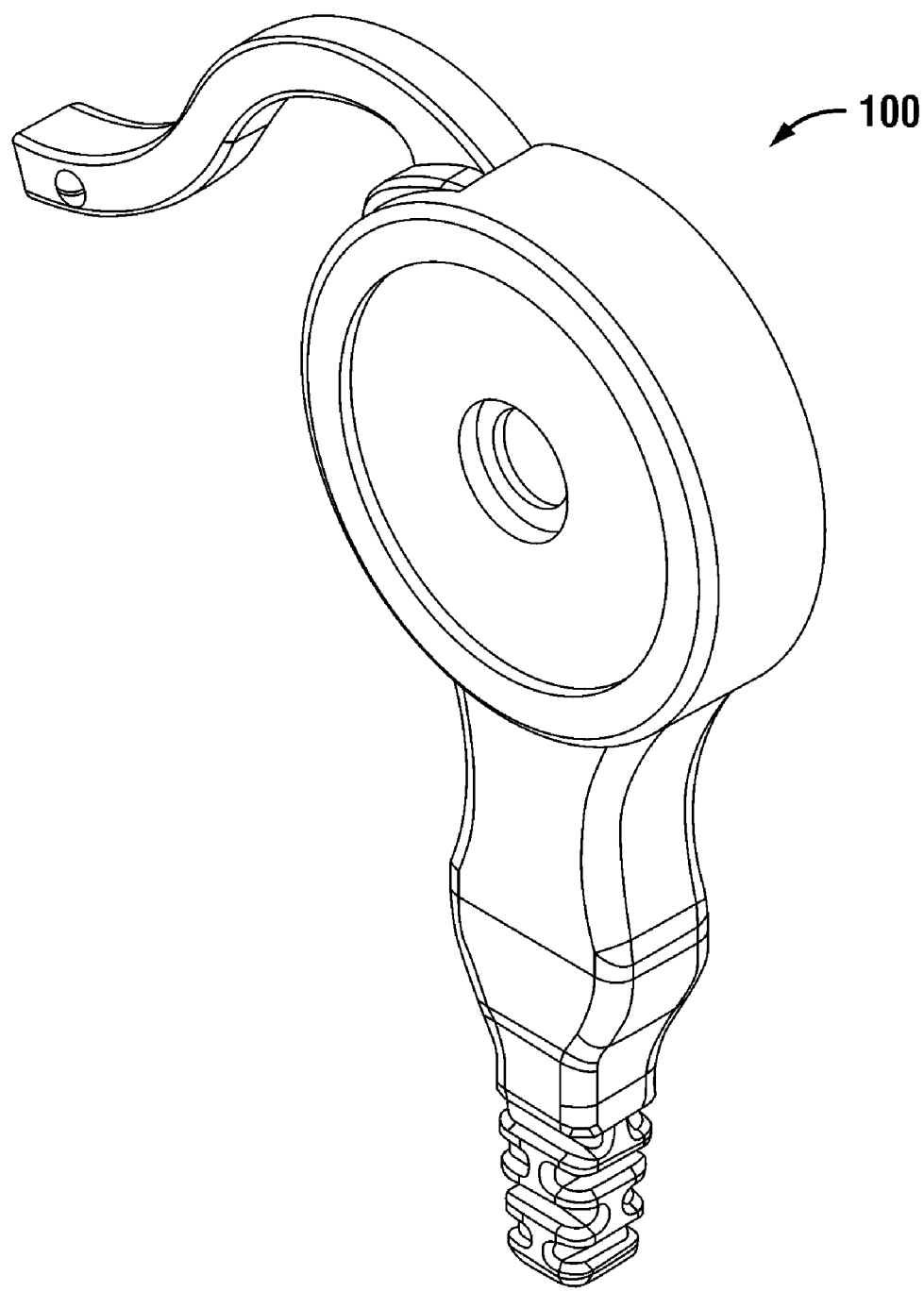
FIG. 3E is an oblique view of the FIG. 1 embodiment of an ECG electrode connector in accordance with the present disclosure.

Referring to FIGS. 1, 2, and 3A, there is shown an embodiment of an ECG electrode connector 100 having a thumb cam lever 110. The connector 100 includes a housing 105 that includes a cavity 106, a pivot pin 115, and a thumb cam lever 110 having a pivot hole 116 defined therein dimensioned to pivotably couple thumb cam lever 110 to pivot pin 115. Connector 100 may also include a cover 305 which optionally includes an identification marking 310 which may be incorporated with cover 305 by any suitable means, including without limitation printing, engraving, silk screening, stamping, or integrally molding said marking 310 onto cover 305. The housing 105, lever 110 and cover 305 may be constructed of any suitable non-conductive material, including without limitation any thermoplastic and/or elastomeric polymer such as polybutylene terephthalate (PBT), polyethylene terephthalate (PET), polyvinyl chloride (PVC), acrylonitrile butadiene styrene (ABS), thermoplastic polyurethanes (TPU), thermoplastic vulcanates (TPV), polypropylene (PP), polyethylene (PE), and/or fiber-reinforced polymer (FRP).

A V-spring 120 having a coil base 130, a fixed leg 131 and a movable leg 132 is coupled to housing 110 within cavity 106. Coil base 130 of V-spring 120 may be multi-turn, single-turn, or a V-shaped apex without a coil. V-spring 120 is retained at its base by pin 117 and is joined to housing 105 at its fixed end by saddle 125 such that movable leg 132 is biased in a distal direction, i.e., towards pivot pin 115. Additionally or alternatively, V-spring 120 may be joined to saddle 125 or cavity 106 by any suitable manner of bonding, such as by adhesive or heat welding. A stop 135 limits the outward flexure of movable leg 132. Thumb cam lever 110 includes a cam 102 which communicates with a detent 140 of spring member 120 when thumb cam lever 120 moves to a closed position, as shown in FIG. 2. Detent 140 and cam 102 cooperate to lock thumb cam lever 110 in a closed position, and additionally or alternatively, provide tactile feedback to a clinician. Additional locking and tactile feedback may be provided by the engagement of a lever detent 160 with a corresponding dimple (not shown) provided on thumb cam lever 110. A lever recess 180 may be provided by housing 105 to receive lever 110 when lever 110 is in the closed position. A finger recess 165 is provided on housing 105 to facilitate manipulation and/or grasping of thumb cam lever 110 by the clinician.

Connector 100 further includes an electrical contact member 155 which is disposed upon cavity 106. Contact member 155 may be constructed from any suitable electrically conductive material, including without limitation stainless steel or low-carbon steel. It is also envisioned contact member 155 may be constructed of a non-conductive material having a conductive coating. Contact member 155 is electrically coupled to a lead wire 175 by any suitable manner of connection, such as a crimp 156, or additionally or alternatively, soldering or wire bonding. Lead wire 175 may optionally be supported at its exit point from housing 105 by a strain relief 170. Contact member 155 provides a contact opening 145 defined therein to accept an electrical contact, such as a bulbous press stud of an ECG pad. In the embodiment, the contact opening 145 may be asymmetrical in shape, such as, for example, an ovoid shape dimensioned at its wide end 151 to accept the bulbous press stud, and dimensioned at its narrow end 150 to capture the narrow waist portion of the press stud. Referring now to FIGS. 3B, 3D, 10A and 10B, the bottom surface 330 of housing 105 provides an aperture 320 disposed therein which exposes contact opening 145 to the exterior of connector 100 to facilitate insertion of a press stud into the connector.

Figure 10A:
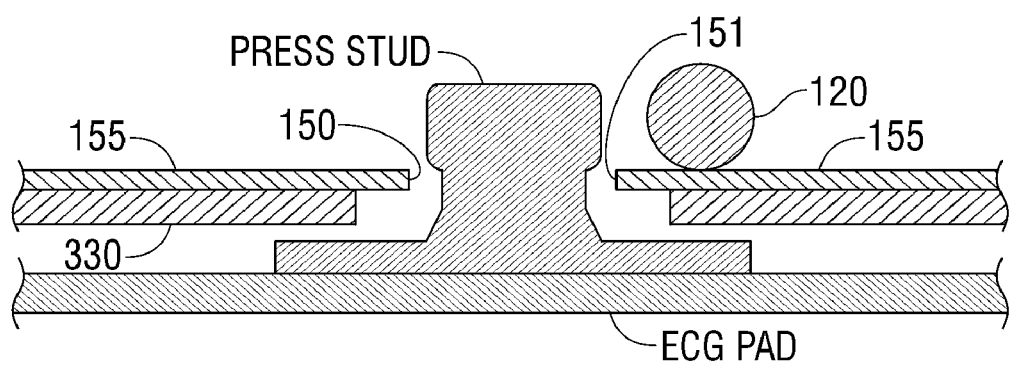
FIG. 10A is an exemplary side detail view of an ECG electrode connector in accordance with the present disclosure disengaged from a press stud of an ECG pad.
Figure 10B:
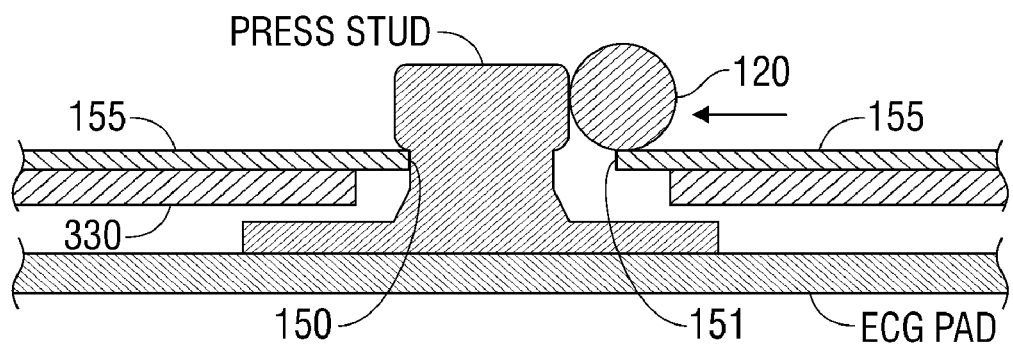
FIG. 10B is an exemplary side detail view of an ECG electrode connector in accordance with the present disclosure engaging a press stud of an ECG pad.
Figure 11A:
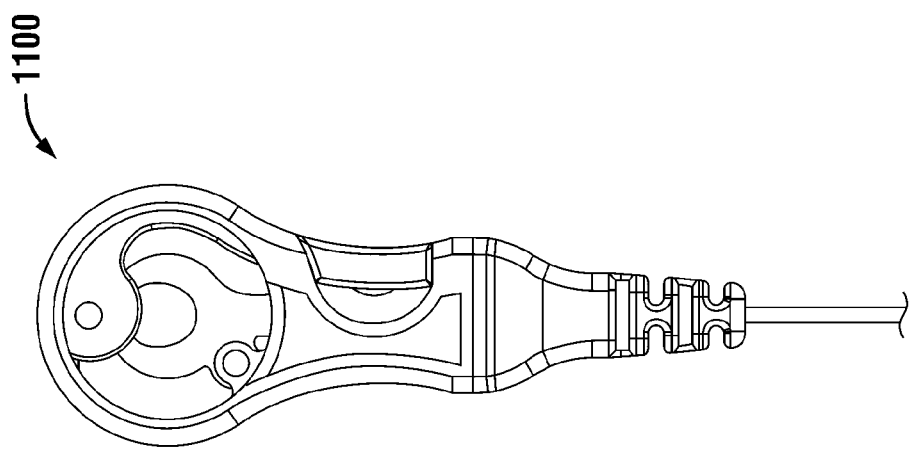
FIG. 11A is a schematic diagram of still another embodiment of an ECG electrode connector in accordance with the present disclosure having a thumb cam lever in a closed position.
Figure 11B:
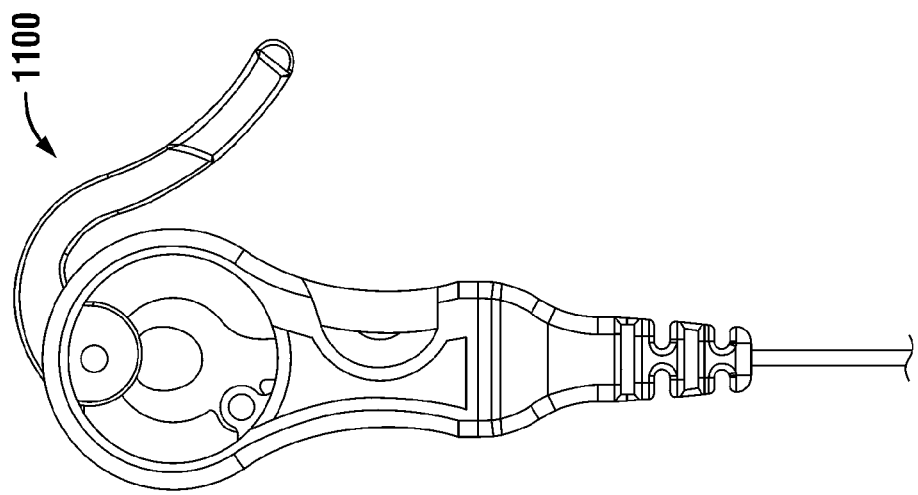
FIG. 11B illustrates the ECG connector of FIG. 11A having a thumb cam lever in an open position in accordance with the present disclosure.
Figure 12A:
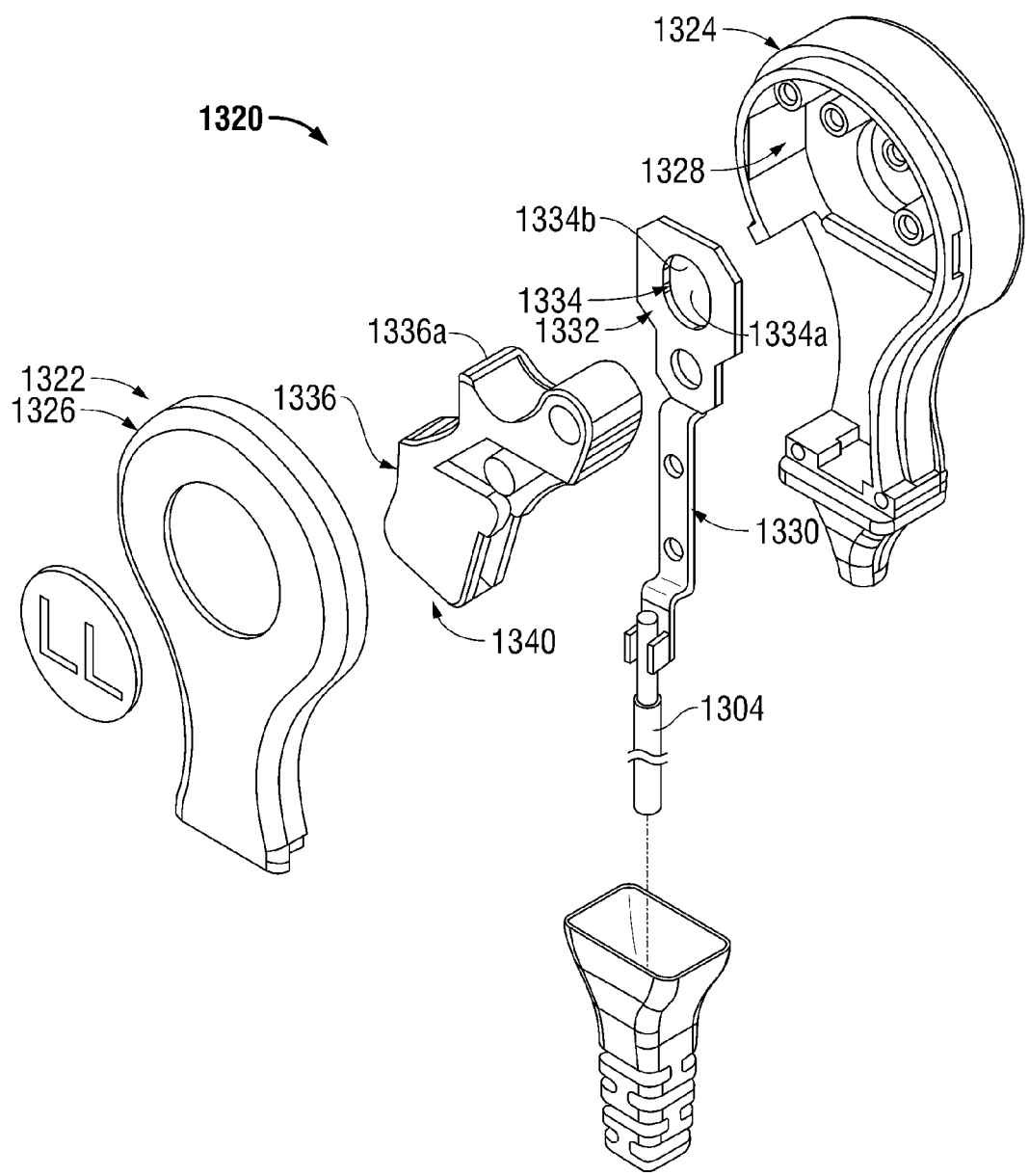
FIG. 12A is an exploded view of a yet another embodiment of an ECG electrode connector in accordance with the present disclosure.
Figure 12B:
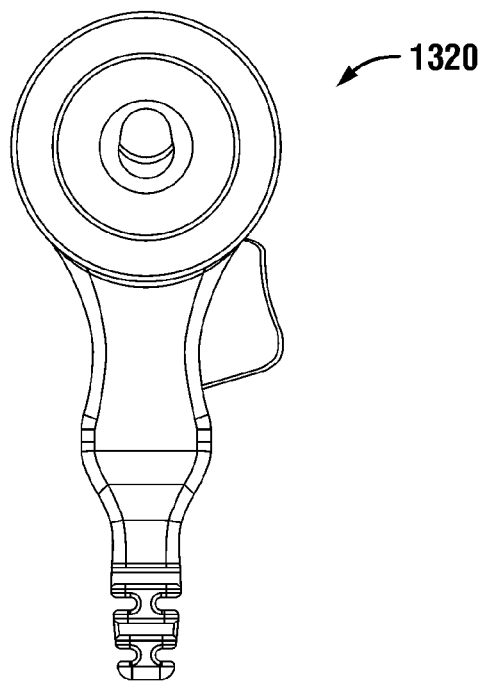
FIG. 12B is a bottom view of the FIG. 12A embodiment of an ECG electrode connector in accordance with the present disclosure.
Figure 12C:
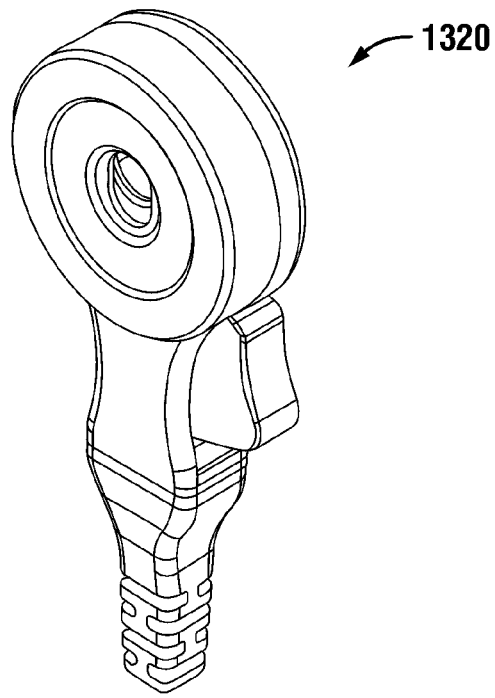
FIG. 12C is an oblique view of the FIG. 12A embodiment of an ECG electrode connector in accordance with the present disclosure.
Figure 13A:
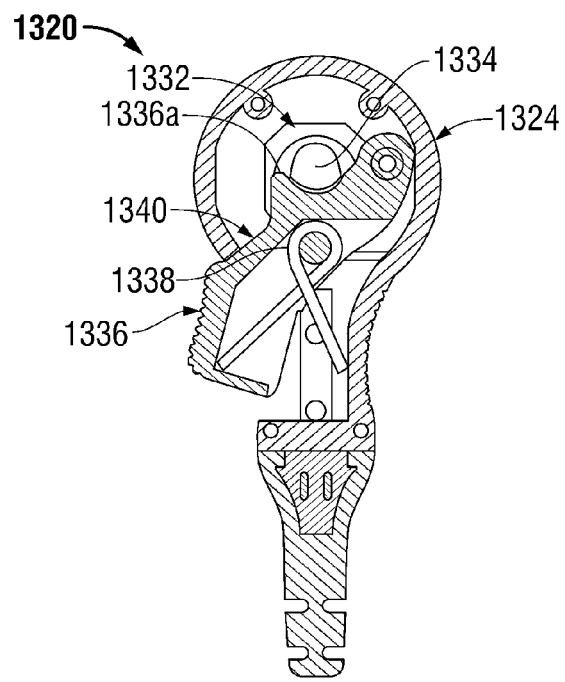
FIG. 13A is a schematic diagram of the FIG. 12A embodiment of an ECG electrode connector in accordance with the present disclosure.
Figure 13B:
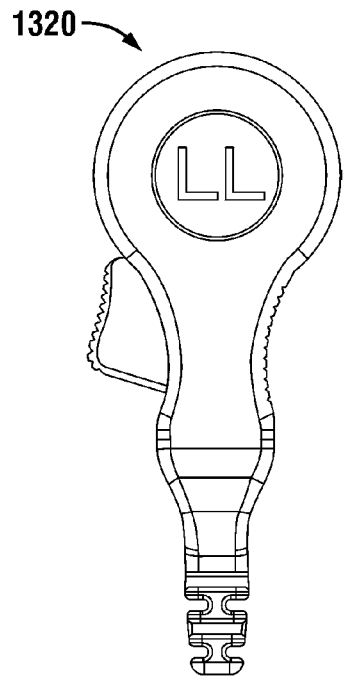
FIG. 13B is a top view of the FIG. 12A embodiment of an ECG electrode connector in accordance with the present disclosure.
Figure 13C:
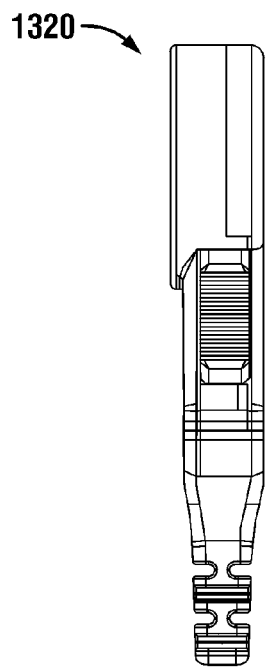
FIG. 13C is a side view of the FIG. 12A embodiment of an ECG electrode connector in accordance with the present disclosure.
Figure 13D:
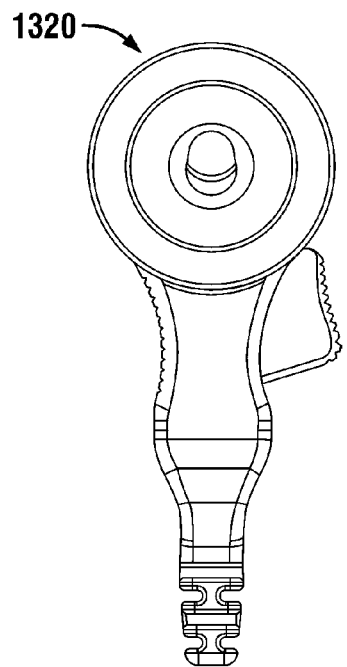
FIG. 13D is a bottom view of the FIG. 12A embodiment of an ECG electrode connector in accordance with the present disclosure.

Engaging a press stud into connector 100 may be accomplished by positioning lever 110 to an open position as shown in FIG. 1, whereupon cam 102 rotates away from detent 140, permitting movable leg 132 of V-spring 120 to flex distally and come to rest upon stop 135. A press stud may then be introduced into connector 100 by, for example, placing connector 100 over a press stud such that the bulbous end press stud is positioned within opening 145, as shown in FIG. 10A. Subsequent to insertion of the press stud, lever 110 may then be moved to the closed position as illustrated in FIG. 2, causing cam 102 to rotate towards moveable leg 132 of V-spring 120. The rotation of cam 102 causes it to ride over detent 140 thereby compressing movable leg 132 in a proximal direction, which mechanically engages and electrically couples the press stud with narrow end 150 of opening 145, as shown in FIG. 10B. Conversely, a press stud engaged with connector 100 as described may be disengaged by moving lever 110 from a closed position to an open position, causing cam 102 to rotate away from detent 140 and relax movable leg 132 of V-spring 120, which disengages the press stud and permits its removal as will be readily appreciated. In another embodiment as shown in FIGS. 11A and 11B in, an ECG electrode connector 1100 is provided wherein a cam is configured to cause mechanical engagement between the press stud and an electrical contact member. A spring may be added to facilitate the opening and actuation of the lever 110.

Turning now to FIGS. 4, 5, 6A, and 6B, another embodiment according to the present disclosure provides an ECG lead wire connector 400 that includes a housing 405 which provides a cavity 406, and a pushbutton 410 having an external face 411 and an internal engaging surface 432. Connector 400 may also include a cover 605 which optionally includes an identification marking 610 as previously described herein. Housing 405, pushbutton 410, cover 605 may be constructed from any suitable non-conductive material as previously described.

Pushbutton 410 is slidably disposed within housing 405 and is biased in a distal direction by a coil spring 420 that is retained at its distal (pushbutton) end by a saddle 426 provided by pushbutton 410, and at its proximal (housing) end by a saddle 425 provided by housing 405. Pushbutton 410 includes at least one stop member 436 which cooperates with stop members 435 and 437 provided within housing 405 to define the distal and proximal limits of travel, respectively, of pushbutton 410. Pushbutton 410 includes an opening 430 disposed therein having an engaging surface 432 for coupling the connector 400 to a press stud as will be further described below.

Connector 400 further includes an electrical contact member 455 which is disposed upon cavity 406. Contact member 455 is electrically coupled to a lead wire 475 by any suitable manner of connection as previously disclosed herein. Lead wire 475 may optionally be supported at its exit point from housing 405 by a strain relief 470. Contact member 455 provides a contact opening 445 defined therein to accept an electrical contact, such as a press stud, and may be an asymmetrical in shape as previously described herein, having a distal narrow end 450 and a proximal wide end 451. The bottom surface 630 of housing 405 provides an aperture 620 disposed therein which exposes contact opening 445 to the exterior of connector 400 to facilitate insertion of a press stud into the connector.

Figure 4:
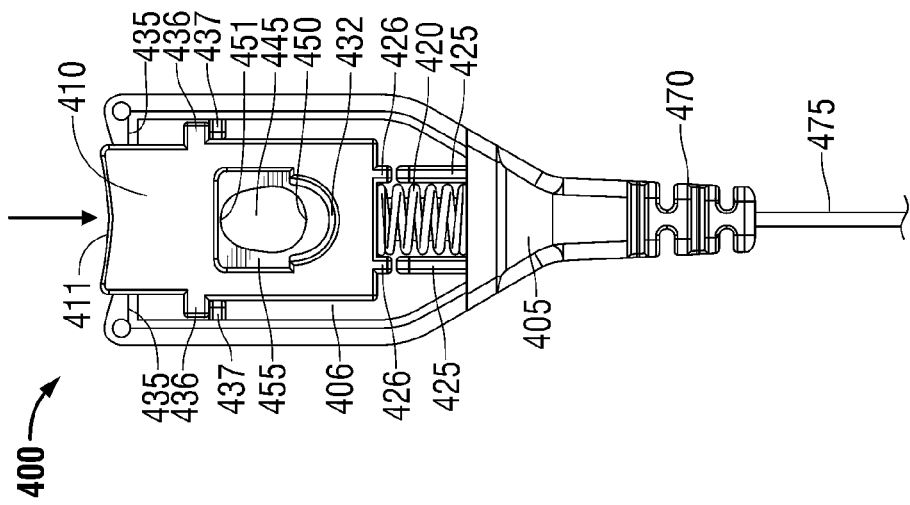
FIG. 4 is a schematic diagram of another embodiment of an ECG electrode connector in accordance with the present disclosure having a pushbutton in a released position.
Figure 5:
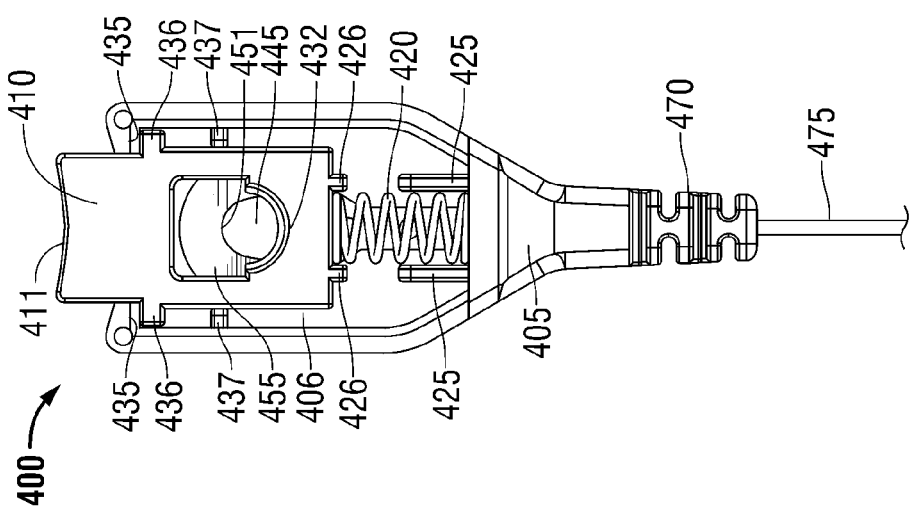
FIG. 5 illustrates the ECG connector of FIG. 4 having a pushbutton in a depressed position in accordance with the present disclosure.
Figure 6B:
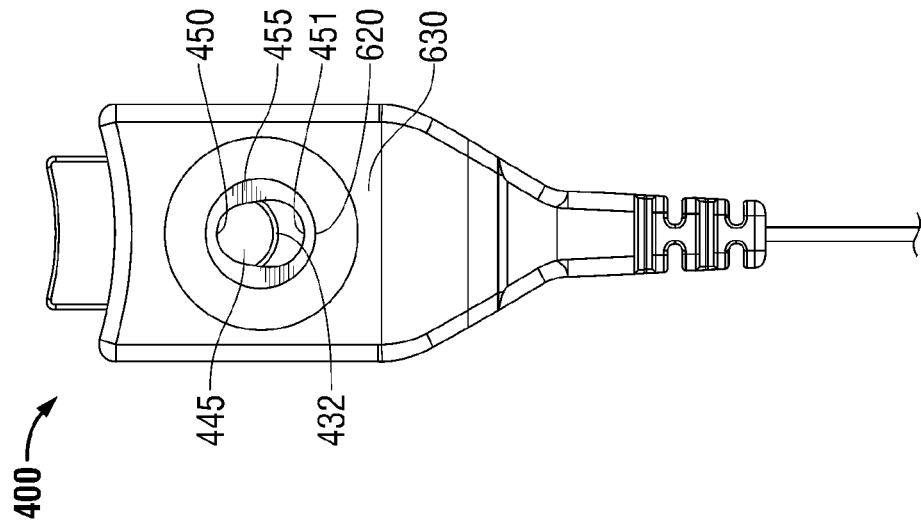
FIG. 6B is a bottom view of the FIG. 4 embodiment of an ECG electrode connector in accordance with the present disclosure.
Figure 6A:
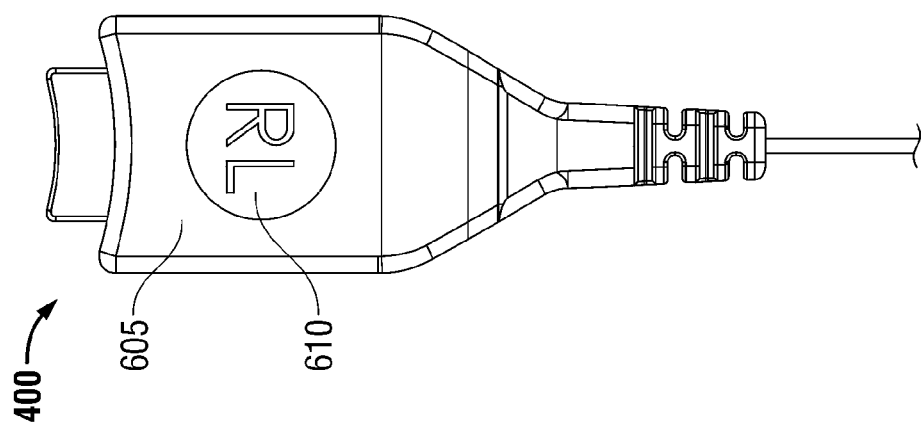
FIG. 6A is a top view of the FIG. 4 embodiment of an ECG electrode connector in accordance with the present disclosure.

Engaging a press stud into connector 400 may be accomplished by depressing pushbutton 410, by, for example, applying sufficient finger pressure to pushbutton face 411 so as to overcome the bias of coil spring 420, thereby moving pushbutton 410 from a distal locked position as shown in FIG. 4 to a proximal open position as shown in FIG. 5. Opening 430 correspondingly moves proximally, exposing the wide proximal end 451 of contact opening 445 and facilitating the insertion of a press stud into connector 400 as best shown in FIG. 6D. Subsequent to insertion of a press stud, pushbutton 410 may then be released whereupon the biasing force of coil spring 420 causes pushbutton 410 to move distally, causing engaging surface 432 to mechanically engage and electrically couple the press stud with narrow end 450 of contact opening 445, as best shown in FIG. 6C. Conversely, a press stud engaged with connector 400 as described may be disengaged by depressing pushbutton 410, causing engaging surface 432 to move proximally, releasing the press stud and facilitating its removal from connector 400. Upon removal of the press stud, pushbutton 410 may be released, readying connector 400 for subsequent use. It is also contemplated in this embodiment to add components, such as linkages or gearing, between pushbutton and electrical contact member to achieve mechanical advantage and improved clamping or connection force.

Yet another embodiment in accordance with the present disclosure is described with reference to FIGS. 7, 8, 9A, and 9B, wherein is shown an ECG lead wire connector 700 having a housing 705 which provides a cavity 706, and a lever 710 pivotally disposed thereupon having an actuating end 715, an external pushbutton face 711, a pivot 712, and an engaging region 716. Connector 700 may also include a cover 905 which optionally includes an identification marking 910 as previously described herein. Housing 705, lever 710, and cover 605 may be constructed from any suitable non-conductive material as previously described herein.

Figure 7:
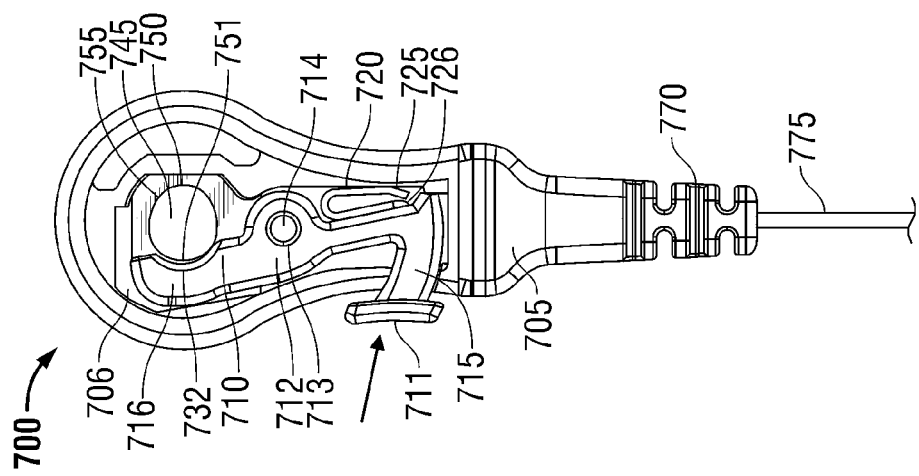
FIG. 7 is a schematic diagram of yet another embodiment of an ECG electrode connector in accordance with the present disclosure having a pivoting lever pushbutton in a released position.
Figure 8:
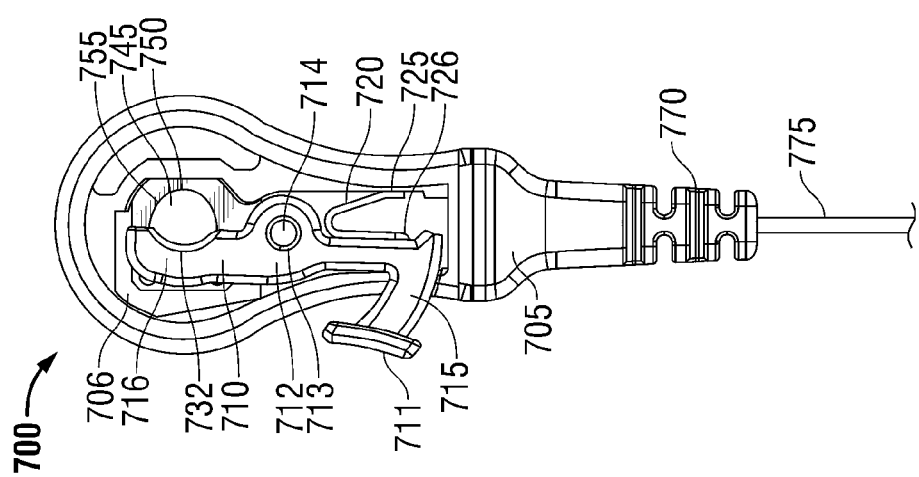
FIG. 8 illustrates the ECG connector of FIG. 7 having a pivoting lever pushbutton in a depressed position in accordance with the present disclosure.

As shown in FIGS. 7 and 8, lever 710 includes a pivot hole 713 disposed therein for pivotally engaging a pivot pin 714 that is provided by housing 705. Actuation end 715 of lever 710 is biased in an outward direction by a leaf spring 720 that is retained at its lever end by surface 726 of lever 710, and at its housing end by a surface 725 of housing 705. Additionally or alternatively, leaf spring 720 may include at least one tab (not shown) retained by at least one slot (not shown) provided by lever surface 726 and/or housing surface 725. Engaging region 716 of lever 710 includes an engaging surface 732 for coupling the connector 700 to a press stud as will be further described below.

Figure 9B:
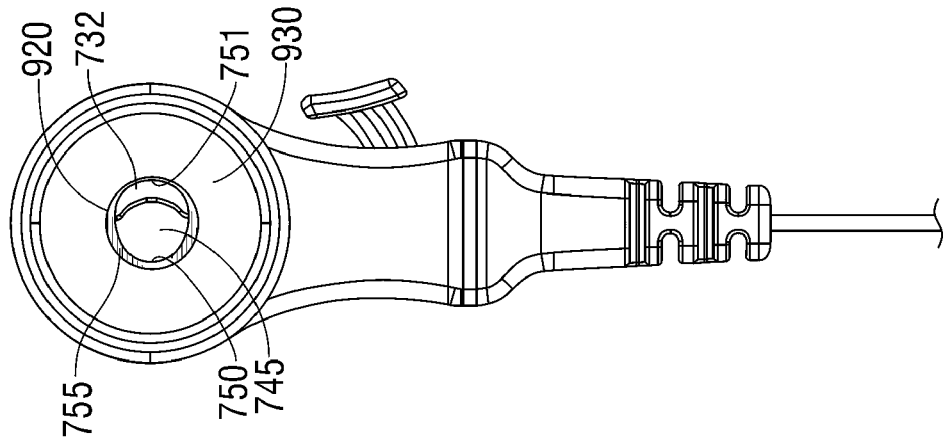
FIG. 9B is a bottom view of the FIG. 7 embodiment of an ECG electrode connector in accordance with the present disclosure.
Figure 9A:
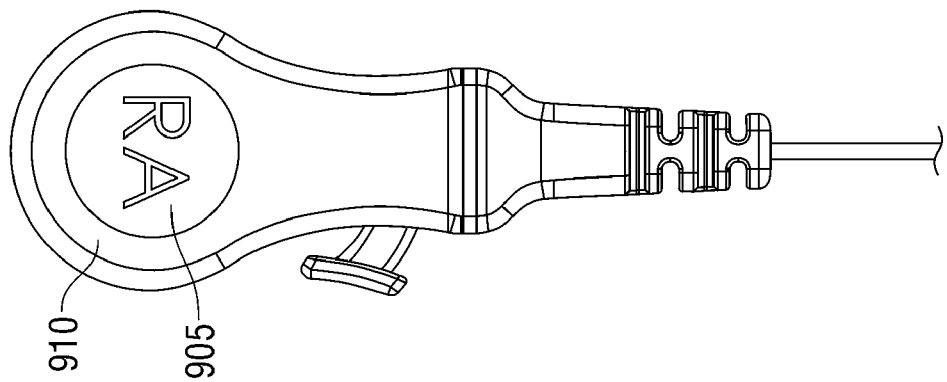
FIG. 9A is a top view of the FIG. 7 embodiment of an ECG electrode connector in accordance with the present disclosure.
Figure 9D:
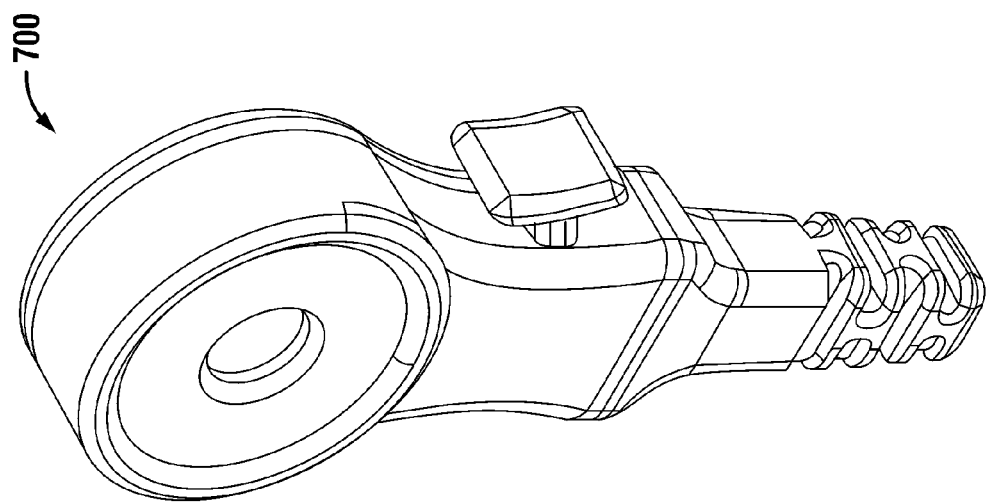
FIG. 9D is an oblique view of the FIG. 7 embodiment of an ECG electrode connector in accordance with the present disclosure.
Figure 9C:
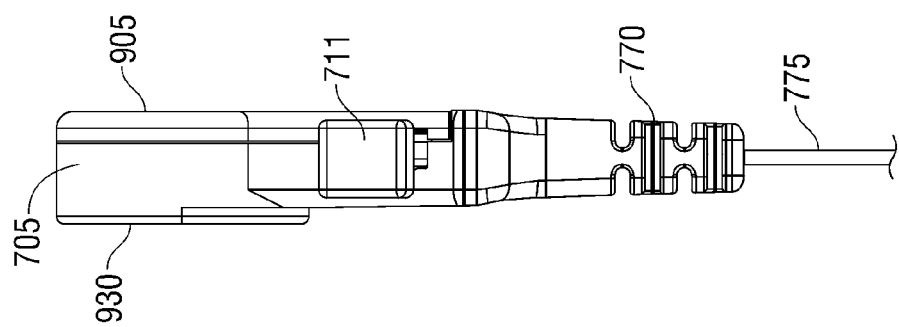
FIG. 9C is a side view of the FIG. 7 embodiment of an ECG electrode connector in accordance with the present disclosure.

Connector 700 further includes an electrical contact member 755 which is disposed upon cavity 706. Contact member 755 is electrically coupled to a lead wire 775 by any suitable manner of connection as previously disclosed herein. Lead wire 775 may optionally be supported at its exit point from housing 705 by a strain relief 770. Contact member 755 provides a contact opening 745 defined therein to accept an electrical contact, such as a press stud, and may be an asymmetrical in shape as previously described herein, having a narrow end 750 and a wide end 751 as best illustrated in FIGS. 8 and 9B. The bottom surface 930 of housing 705 provides an aperture 920 disposed therein which exposes contact opening 745 to the exterior of connector 700 to facilitate insertion of a press stud into the connector.

Engaging a press stud into connector 700 may be accomplished by depressing pushbutton face 711, by, for example, applying sufficient finger pressure thereto so as to overcome the bias of leaf spring 720, thereby causing engaging region 716 of lever 710 to swing from a closed position as shown in FIG. 7 to an open position as shown in FIG. 8. The wide end 751 of contact opening 745 is thereby exposed thus facilitating the insertion of a press stud into connector 700. Pushbutton face 711 may then be released whereupon the biasing force of leaf spring 720 causes engaging surface 732 to move toward the inserted press stud to mechanically engage and electrically couple the press stud with narrow end 750 of contact opening 745, as will be readily appreciated. Conversely, a press stud engaged with connector 700 as described may be disengaged by depressing pushbutton 710, causing engaging surface 732 to swing away from the press stud (i.e., away from narrow end 750 of contact opening 745), releasing the press stud and facilitating its removal from connector 700. Upon removal of the press stud, pushbutton face 711 may then be released, readying connector 700 for subsequent use.

With reference now to FIGS. 12A-C and FIGS. 13 A-D, an embodiment of an ECG electrode connector 1320 includes a housing 1322 having an upper member 1324 and a lower member 1326, and defining an internal cavity 1328 therebetween. Housing 1322 is fabricated from a non-conducting material, e.g., an injection molded polymer which electrically insulates the subject from the conductive element(s) therewithin. Upper member 1324 and lower member 1326 are separate components attached to each other by any suitable method of bonding, such as without limitation, adhesive, ultrasonic welding, or heat welding. Upper member 1324 and lower member 1326 form a non-conductive element of the housing 1322.

Housing 1322 includes a lead wire terminal 1330 which is electrically connected to a respective end of lead wire 1304 by any suitable method of connection, including without limitation, crimping, soldering, or welding. Housing 1322 supports a contact member 1332 that is electrically connected to lead wire terminal 1330. Contact member 1332 and lead wire terminal 1330 may be integrally formed. Contact member 1332 defines a contact opening 1334 formed therein and in communication with internal cavity 1328 of housing 1322. Contact opening 1334 includes first contact opening portion 1334a and second contact opening portion 1334b. First contact opening portion 1334a defines an internal dimension or diameter which is greater than the corresponding internal dimension or diameter of second contact opening portion 1334b.

Housing 1322 further includes a lever 1340 pivotably connected thereto. Lever 1340 includes an actuating end 1336. Lever 1340 is biased to a first position by a biasing member 1338. Lever 1340 includes an engaging region 1336a projecting therefrom so as to extend across first contact opening portion 1334a of contact opening 1334 when lever 1340 is in the first position. In use, lever 1340 is actuatable to a second position wherein engaging region 1336a thereof does not obstruct or extend across first contact opening portion 1334a of contact opening 1334. For example, a clinician may apply finger pressure to actuating end 1336 that is sufficient to overcome the biasing force of biasing member 1338, thereby causing engaging region 1336a to move to a second position as herein described.

ECG electrode connector 1320 is adapted for connection to a conventional snap-type biomedical electrode (not explicitly shown). A typical snap-type biomedical electrode incorporates an electrode flange or base and male press stud or terminal extending in transverse relation to the electrode base. The male press stud terminal may have a bulbous head whereby an upper portion of the terminal has a greater cross-sectional dimension than a lower portion of the terminal. Accordingly, in use, when lever 1340 of electrode connector 1320 is in the second position, the head of the male press stud terminal of the snap-type biomedical electrode may be inserted into first contact opening portion 1334a of contact opening 1334 and actuating end 1336, and thus, lever 1340, may be released so that biasing member 1338 moves engaging region 1336a of lever 1340 against the head of the male press stud (not explicitly shown) to push or force the lower portion of the press stud into a second contact opening portion 1334b of contact opening 1334. The biasing force of biasing member 1338 helps to maintain the press stud within second contact opening portion 1334b of contact opening 1334 and thus inhibits removal or disconnection of the biomedical electrode from ECG connector 1320.

It will be understood that various modifications may be made to the embodiments disclosed herein. Further variations of the above-disclosed and other features and functions, or alternatives thereof, may be desirably combined into many other different systems, instruments and applications. Various presently unforeseen or unanticipated alternatives, modifications, variations or improvements therein may be subsequently made by those skilled in the art, which are also intended to be encompassed by the following claims.

What is claimed is:

1. An ECG connector assembly, comprising:
   a housing having a first opening disposed therein dimensioned to operably receive the press stud of an ECG electrode pad;
   an electrical contact member defining a contact plane and having a second opening disposed therein, the second opening disposed substantially concentrically to the first opening, wherein the perimeter of the second opening is less than the perimeter of the first opening;
   a resilient member having a movable leg and a fixed leg, wherein the movable leg has at least a relaxed position and a compressed position, the movable leg being configured in its compressed position to operably engage a narrow waist portion of the press stud and further configured to couple the narrow waist portion of the press stud with the electrical contact member; and
   a lever pivotably coupled to the housing and having at least an open position and a closed position, wherein the lever is pivotable about an axis orthogonal to the contact plane and includes a cam configured to cause the resilient member to move to its compressed position when the lever is in the closed position.

2. An ECG connector assembly in accordance with claim 1, wherein the movable leg of the resilient member includes a detent configured to cooperatively engage the cam to retain the lever in the closed position.

3. An ECG connector assembly, comprising:
   a housing having a first opening disposed therein dimensioned to operably receive the press stud of an ECG electrode pad;
   an electrical contact member defining a contact plane and having a second opening disposed therein, the second opening disposed substantially concentrically to the first opening, wherein the perimeter of the second opening is less than the perimeter of the first opening; and
   a lever pivotable about an axis orthogonal to the contact plane and disposed within the housing and having at least an engaged position and a disengaged position, wherein the lever further includes an actuating end, an engaging region, and a pivot, the engaging region configured to operably engage a narrow waist portion of the press stud and further configured to couple the narrow waist portion of the press stud with the electrical contact member when the lever is in the engaged position.

4. An ECG connector assembly, comprising:
   a housing having a first opening disposed therein dimensioned to operably receive the press stud of an ECG electrode pad;
   an electrical contact member defining a contact plane and having a second opening disposed therein, the second opening disposed substantially concentrically to the first opening, wherein the perimeter of the second opening is less than the perimeter of the first opening; and a lever pivotably coupled to the housing about an axis orthogonal to the contact plane and having at least an open position and a closed position, wherein the lever includes a cam configured to operably engage a narrow waist portion of the press stud and further configured to couple the narrow waist portion of the press stud with the electrical contact member when the lever is in the closed position.

5. The ECG connector assembly in accordance with any of claims 1, 3, and 4, wherein the second opening has a shape selected from the group consisting of ovoid shaped, pear-shaped, keyhole-shaped, circular, and a shape described by the intersection of two partially-coincident circles.

6. The ECG connector assembly in accordance with any of claims 1, 3, and 4, wherein the electrical contact member is constructed from material selected from the group consisting of stainless steel and low-carbon steel.

7. The ECG connector assembly in accordance with any of claims 1, 3, and 4, wherein the housing is constructed from electrically non-conducting material.

8. The ECG connector assembly in accordance with claim 7, wherein the housing material is selected from the group consisting of polybutylene terephthalate, polyethylene terephthalate, polyvinyl chloride, acrylonitrile butadiene styrene, polyethylene, polypropylene, thermoplastic urethanes, thermoplastic elastomers, and fiber-reinforced polymers.

9. The ECG connector assembly in accordance with any of claims 1, 3, and 4, further comprising:

a lead wire having a proximal end and a distal end, wherein the distal end thereof is electrically coupled to the electrical contact member; and a strain relief included with the housing and having at least part of the lead wire disposed therethrough.

10. The ECG connector assembly in accordance with claim 9, wherein the coupling of the lead wire to the electrical contact member is selected from the group consisting of a solder connection, a crimp connection, a welded connection, and a wire bond connection.

11. The ECG connector assembly in accordance with any of claims 1 and 4, further comprising:

a lever recess provided within the housing dimensioned to receive at least part of the lever while the lever is positioned in a closed position.

12. The ECG connector assembly in accordance with claim 11, further comprising:

a detent provided within the lever recess; and a dimple, corresponding to the detent, provided on the lever;

wherein the detent and dimple engage to retain the lever while the lever is positioned in a closed position.

13. The ECG connector assembly in accordance with claim 11, further comprising a finger recess provided within the housing and disposed substantially adjacently to a proximal end of the lever recess.

* * * * *

UNITED STATES PATENT AND TRADEMARK OFFICE
Certificate

Patent No. 8,038,484 B2                                                                   Patented: October 18, 2011

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: David Selvitelli, Suffield, CT (US); Peter Meyer, Shrewsbury, MA (US); and Peter Yu, Shenzhen (CN).

Signed and Sealed this Twenty-fifth Day of March 2014.

*RENEE LUEBKE*
*Supervisory Patent Examiner*
*Art Unit 2833*
*Technology Center 2800*